United States Patent [19]
Junior

[11] Patent Number: 6,139,529
[45] Date of Patent: Oct. 31, 2000

[54] ADVANCED ANESTHETIC METHOD

[76] Inventor: Alceu Meibach Rosa Junior, Rua da Contagem, 206-Saúde, São Paulo, SP CEP 04.146-100, Brazil

[21] Appl. No.: 09/325,908

[22] Filed: Jun. 4, 1999

Related U.S. Application Data

[63] Continuation-in-part of application No. 09/113,843, Jul. 7, 1998, abandoned.

[51] Int. Cl.⁷ .................................................. A61M 37/00
[52] U.S. Cl. ............................... 604/131; 604/30; 604/65
[58] Field of Search ..................................... 604/131, 151, 604/187, 207, 30, 65, 66, 67, 500; 128/DIG. 1

[56] References Cited

U.S. PATENT DOCUMENTS

| | | |
|---|---|---|
| 4,613,328 | 9/1986 | Boyd ........................................ 604/156 |
| 4,747,824 | 5/1988 | Spinéllo . |
| 4,787,893 | 11/1988 | Villete ...................................... 604/188 |
| 5,176,646 | 1/1993 | Kuroda ..................................... 604/154 |
| 5,456,670 | 10/1995 | Neer et al. ............................... 604/155 |
| 5,647,851 | 7/1997 | Pokras ...................................... 604/131 |
| 5,672,155 | 9/1997 | Riley et al. .............................. 604/154 |
| 5,690,618 | 11/1997 | Smith et al. ......................... 604/207 X |

*Primary Examiner*—John D. Yasko
*Attorney, Agent, or Firm*—Schweitzer Cornman Gross & Bondell LLP

[57] ABSTRACT

An advanced osseous or periosseous dental anesthetic method involving apparatus for motorized injection of anesthetic liquids at a low and extended volumetric rate. The anesthetic is injected at a low and extended volumetric rate adjacent or directly into the osseous without pain or danger to the surrounding tissue.

6 Claims, 7 Drawing Sheets

ADVANCED ANESTHETIC METHOD

RELATED APPLICATION

This is a continuation-in-part of pending U.S. patent application Ser. No. 09/113,843, filed Jul. 7, 1998 now abandoned.

FIELD OF THE INVENTION

The invention pertains to the field of medical liquid anesthetic methods and, in particular, to medical anesthetic methods using liquid injectors having precise and controllable flow rates.

BACKGROUND AND SUMMARY OF THE INVENTION

While the purpose of dental anesthesiology is to maintain the comfort of the patient and to allow proper treatment of the patient, it is traditionally associated with suffering and discomfort. In fact, dental professionals have observed that anesthetic injection commonly results in negative reactions and anxiety in patients, especially children.

The traditional device for injecting anesthetic solutions has been the manual syringe. The manual syringe has been a relatively effective device for administering anesthesia. However, since the syringe is operated manually, the rate and force of the injection vary.

The method of this invention overcomes the limitations of the traditional methods by employing a precisely controllable programmable medical liquid injector.

In a first embodiment of the method, the tissue is topically anesthetized in the region of puncture. Then, after a few seconds, a few drops of anesthetic are injected in the gingival papilla (for inferior molars) or, in the limit between the attached and the free gingiva (for other teeth), through the needle of preferably a programmable injector. The needle is then removed and then reinserted slowly, after the anesthetic has taken effect, into the alveolar crest (for the inferior molars) or, into the subperiosteal, next to the radicular apex (for the other teeth), while maintaining the anesthetic flow rate at approximately 0.3 ml per minute.

In a second embodiment of the method, the needle of the programmable injector penetrates the periosteum and the anesthetic is injected under the periosteum. This subperiosteal anesthetic technique generally requires a low quantity of anesthetic, which is desirable to minimize toxicity and other possible negative effects of the anesthetic, and to decrease the time require for post-operative recovery.

Prior known subperiosteal anesthesia techniques can result in distension of the periosteum. Specifically, with prior techniques, subperiosteal injections can cause a detachment of the periosteum from the subjacent osseous layer to which the periosteum is firmly attached. Other possible negative effects include ischemia and necrosis of the periosteum tissue. These effects can cause instant, as well as post-operative pain.

For the above reasons, doctors have heretofore avoided subperiosteal anesthesia, preferring supraperiosteal anesthesia. Doctors have considered subperiosteal anesthetic injection a "complementary" technique only to be used if other "conventional" techniques are unavailable.

Studies on the administration of anesthetic determined a close relationship between dosage requirements and effectiveness, and the velocities of administration of the anesthetic drug. It has been determined that excessively rapid or large injections can tear away tissues due to excessive pressure, causing inflamed areas and necrosis in the tissue, as well as discomfort to the patient.

The recommendation is that one should make soft and continuous movements, not just in the needle introduction but also during the administration of the anesthetic drug. However, due to the various levels of skill and dexterity of dental professionals using traditional equipment, such as the manual carpule, it is often not possible to achieve soft and continuous movements on a consistent basis.

A computerized system of anesthetic injection is marketed under the name Control-Inject. This device allows precise speed control of anesthetic injection, and due to its computerized speed control system, has given the possibility, through studies, to find the ideal speed of anesthetic injection for different situations usually found at the dental office. So far, these studies have brought new results of great importance for the comprehension of the anesthetic's physiology in the human body.

One of these new results is based on the relationship between the speed of injection and the osseous tissue's capability of absorbing the anesthetic liquid when applied in the bone or in the periosteum. Before the invention of the Control-Inject anesthetic injector, it was thought that all the applications in osseous sites unavoidably would present strong pain, caused by the tearing away of the periosteum during the deposition of the anesthetic solution. With the resources from this injector, it was determined that, at the constant velocity of 0.3 ml per minute, all the volume deposition in the osseous site is absorbed by the bone. Thus, the periosteum does not tear away, enabling a painless injection either during the application or post-operative.

Besides that, the fact that there is no anesthetic reflux, and all the deposited volume is completely utilized, allows a great reduction in the dose required in the dental treatment. Small doses mean small risks. Injection at the controlled slow speed makes the traditional painful applications like the ones applied at the palate, the subperiosteal and intraligamentary injections, much more comfortable for the patient.

Recognition of the uniformity of good performance in osseous or periosseous anesthetic application techniques resulting from injection of anesthetic at a maximum rate of 0.3 ml per minute made possible the development of a practical, compact and simplified anesthetic injector which is the subject of patent application Ser. No. 09/113,843 filed Jul. 10, 1998.

DETAILED DESCRIPTION OF THE INVENTION

Figure 1:
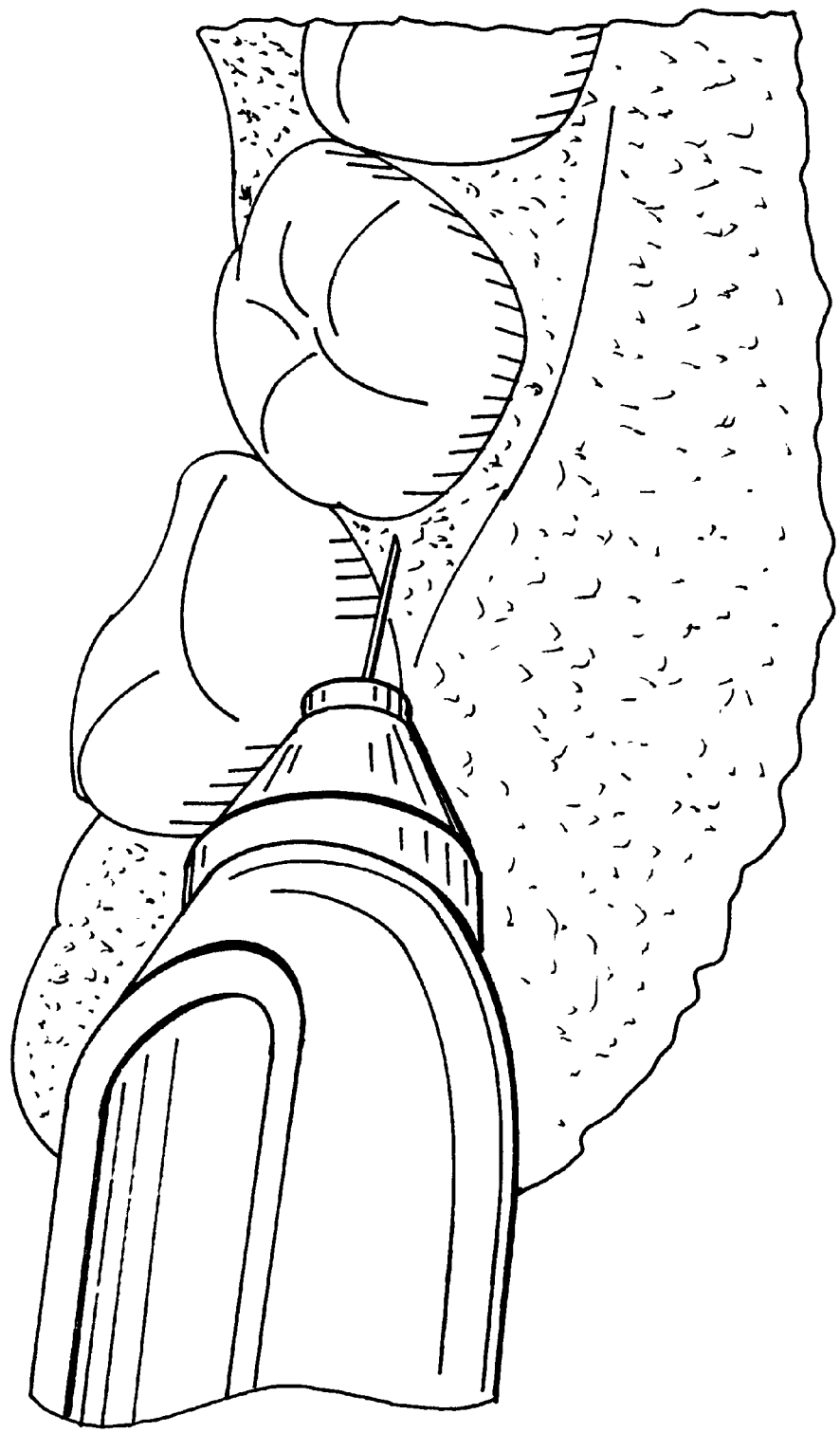
FIG. 1 is a view of a needle inserted into the preferred access point of the gingival papilla.

In a first embodiment of the dental procedure according to the present invention, suitable for the anesthesia of inferior molars, the access is preferably made from the buccal side. The point of access preferably is the center of a vertical axis between the apex of the gingival papilla and its base. This is a little higher up than with the prior intraseptal technique, in which access is from a position approximately 4 mm from the gingival papilla (papilla apex), corresponding generally to its base. The new procedure enables reaching the osseous crest. This access point is equidistant from the adjacent teeth. In other words, if one imagines the gingival papilla being the figure of a triangle, the perforation of the needle will be in its center (see FIG. 1).

Figure 2:
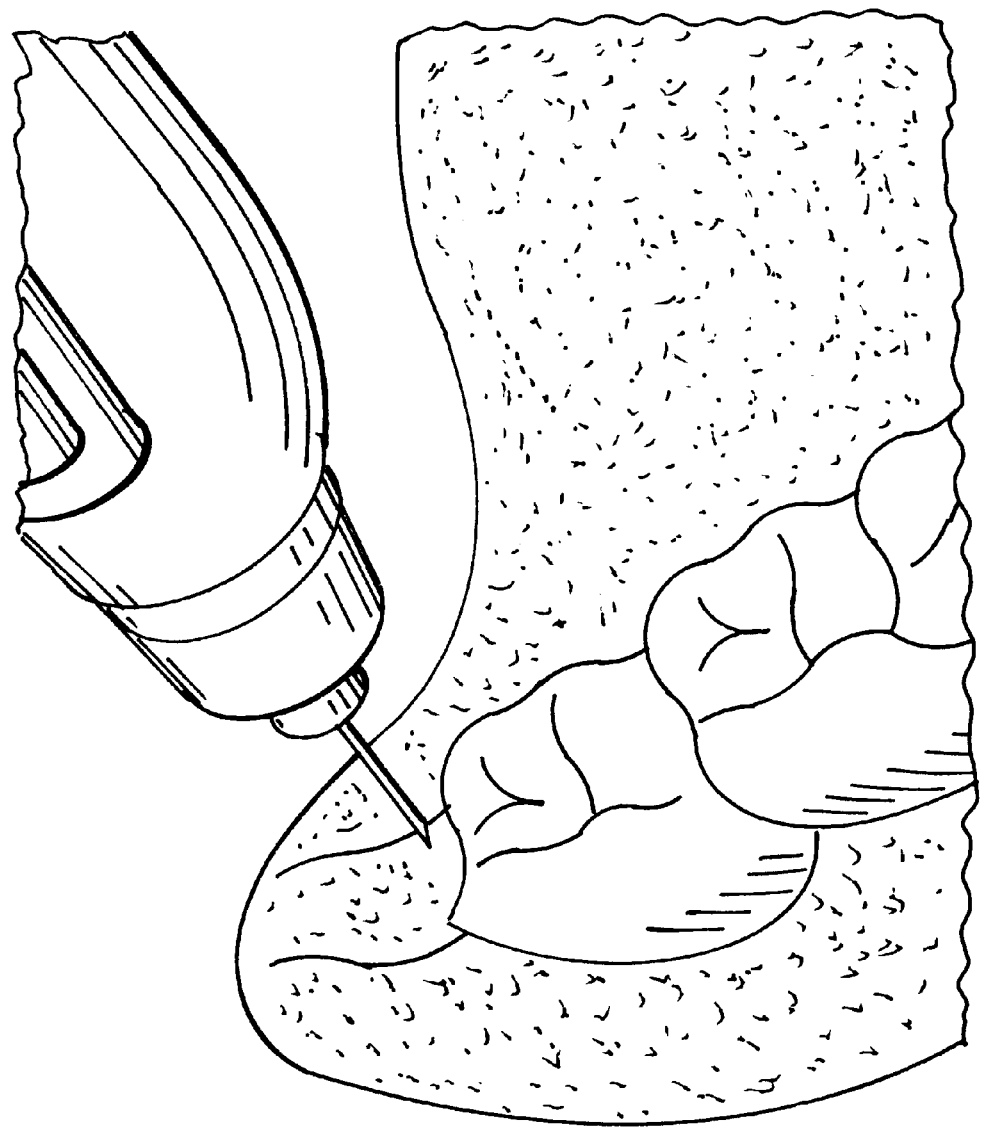
FIG. 2 is a view of a needle inserted into an alternate access point.

For second or third molars, where the limit of the labial commissure interferes with the placement of the needle through the buccal side, the access can be inverted to the lingual (FIG. 2), searching the same target of the osseous crest.

Figure 3:
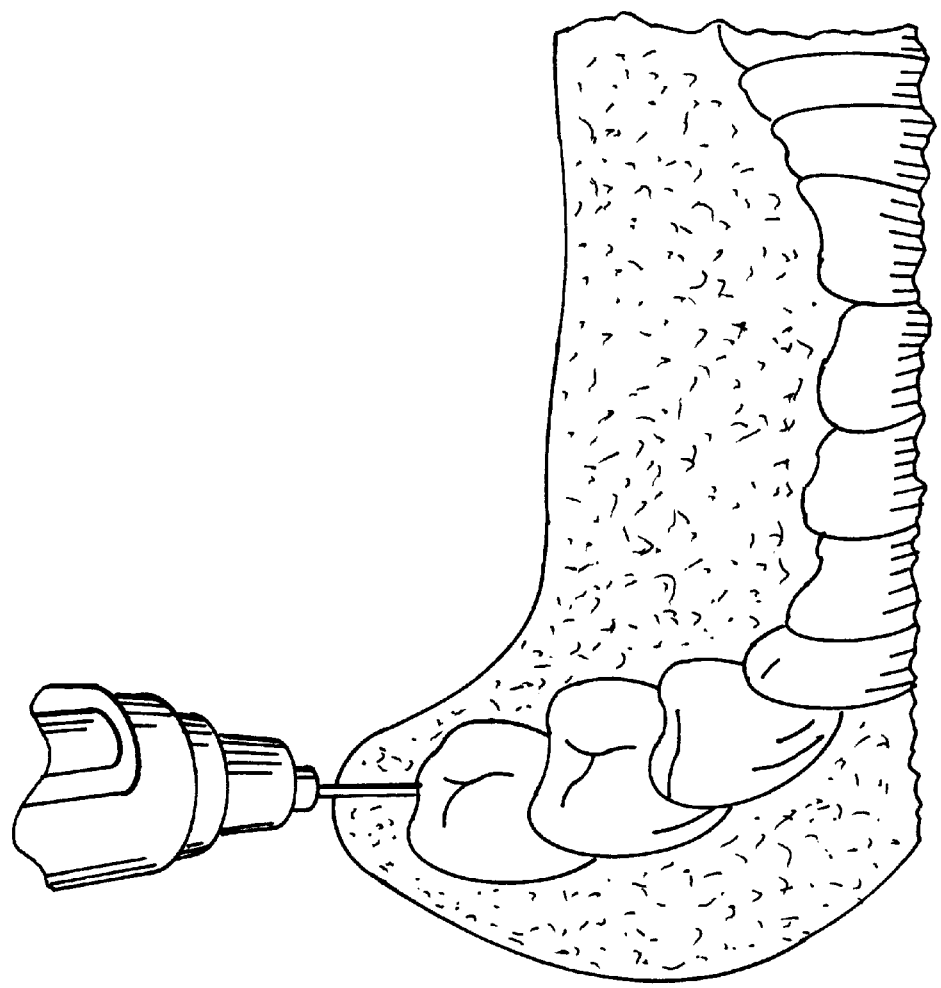
FIG. 3 is a view of a needle inserted at an antero-posterior angle.

For second molars of patients who do not have third molars (e.g., from anodontia or exodontics), or for third molars, the needle can be placed in the anteroposterior angle (FIG. 3), just behind the last tooth at issue, or through the lingual face.

Figure 4:
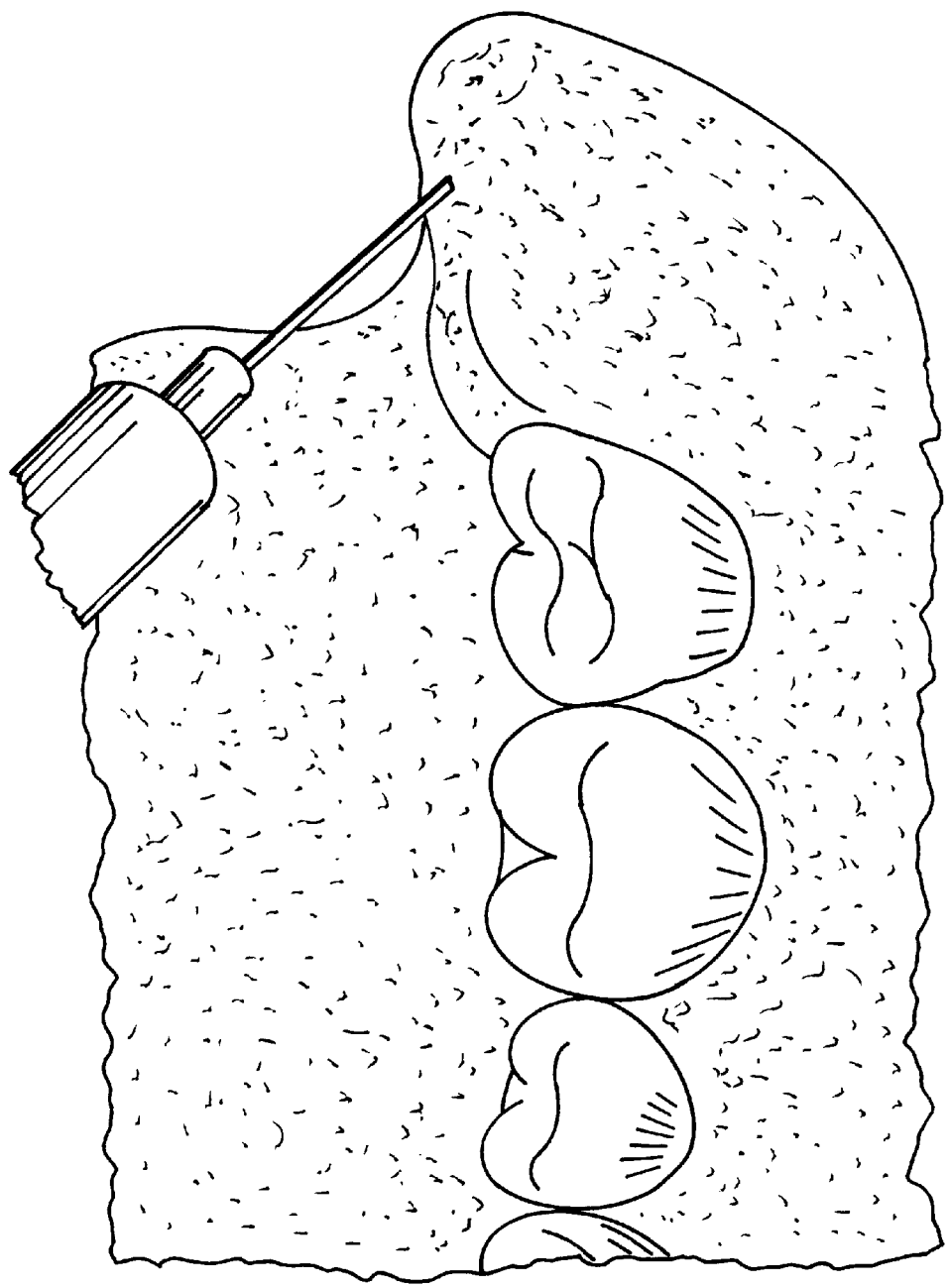
FIG. 4 is a view of a needle inserted behind the third molar.

For second molars in young patients, whose third molars have not yet cut, but that can nevertheless prevent penetration of the needle, the access can be any of those previously described; the perforation should be just behind an imaginary measure, corresponding to what should be the place of the third molar if it were present (FIG. 4).

It should be noted that it is not advisable to bend the needle to facilitate its access. This maneuver diminishes its power of penetration in the alveolar crest.

In the new technique, anesthesia is only applied in the papilla distal to the tooth to be anesthetized, even in molar cases.

In the known intra-septal technique, the anesthetic solution is placed beneath the external cortical plate, close to the alveolar crest, and the deposition is always intro-osseous. As this point is more distant to the apex of the papilla than the one utilized in the new technique of the invention, it is difficult to penetrate the needle through the external cortical plate, typically requiring a previous perforation with special drills (trepans). Typically, a dental engine is used for this work. This technique has been generally abandoned because of the operative difficulties with risks presented by the possibility of fracturing drills or traumatism to the roots of the teeth, the need of preparation and previous sterilization of the specific instruments, as well as the time required.

Figure 5:
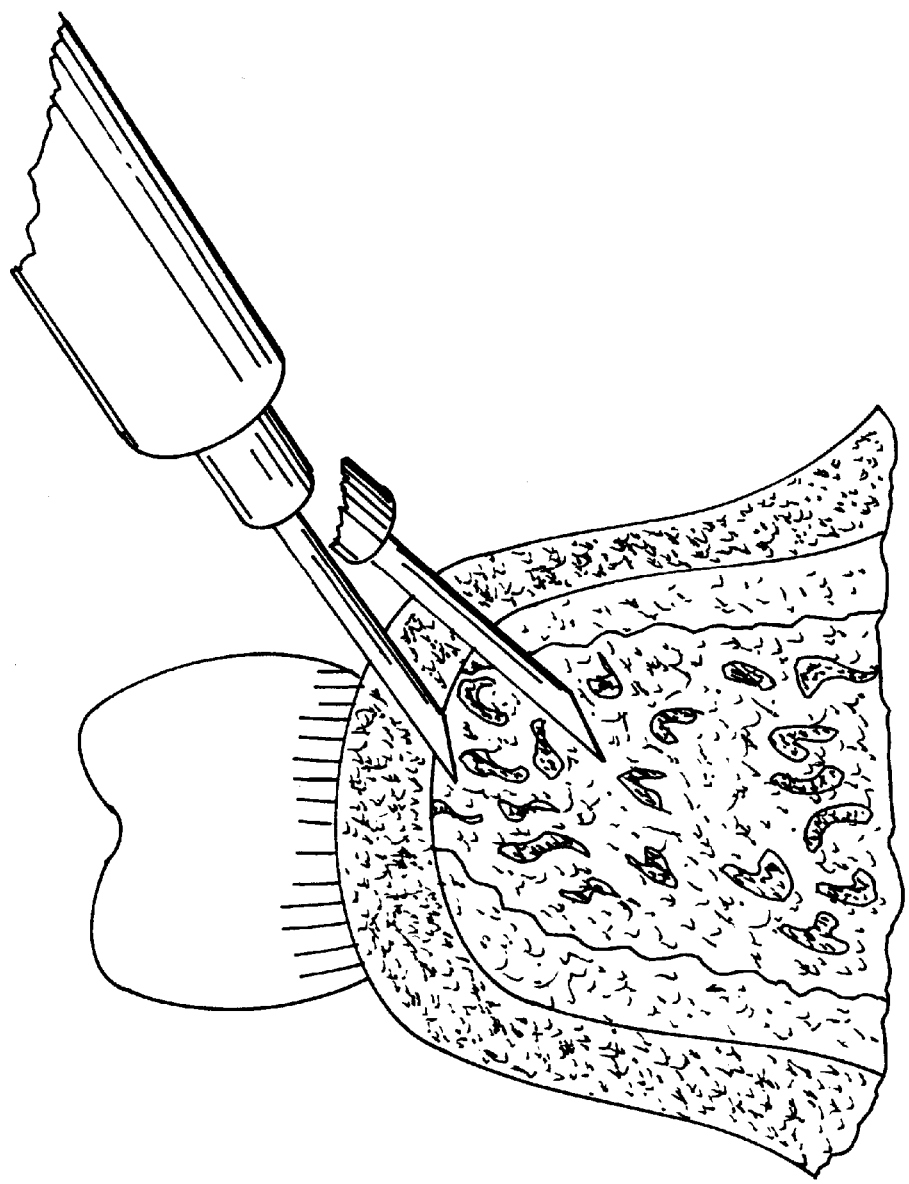
FIG. 5 is a view of a needle inserted into the alveolar crest.

In the technique of the invention, the anesthetic is placed in the alveolar crest, between the buccal and lingual sides, slightly above the placement in the intra-septal technique (FIG. 5). The deposition can be subperiosteal or intra-osseous; the latter, however, does not require a previous perforation on the bony crest with drills (trepans), being done by just forcing the tip of the needle (preferably a short needle) in the right part. In pediatrics, this procedure is not difficult because the children have a cortical plate less thick than the adults. The point of anesthetic deposition (alveolar crest) is, in fact, represented by a part of reduced dimension which has the characteristic of being permeable to the penetration of the anesthetic solution.

In cases where the needle will not penetrate into the osseous crest, but contact with the crest is still possible, results were found to be similar to the cases in which the penetration was effected (this fact has been shown mainly for molars). The failure of block has been noted only in cases in which the needle did not touch the bone and the exact subperiosteal position had not been reached.

The method results in an important hydraulic behavior: the low and precisely controlled speed of application, allied to the strength of the injection, results in an effective utilization of the entire quantity of anesthetic solution, infiltrated into the bone, without reflux. This fact remarkably increases the anesthesia efficiency time and has made it possible to more efficiently relate the duration time of the block and the dose applied.

Figure 6:
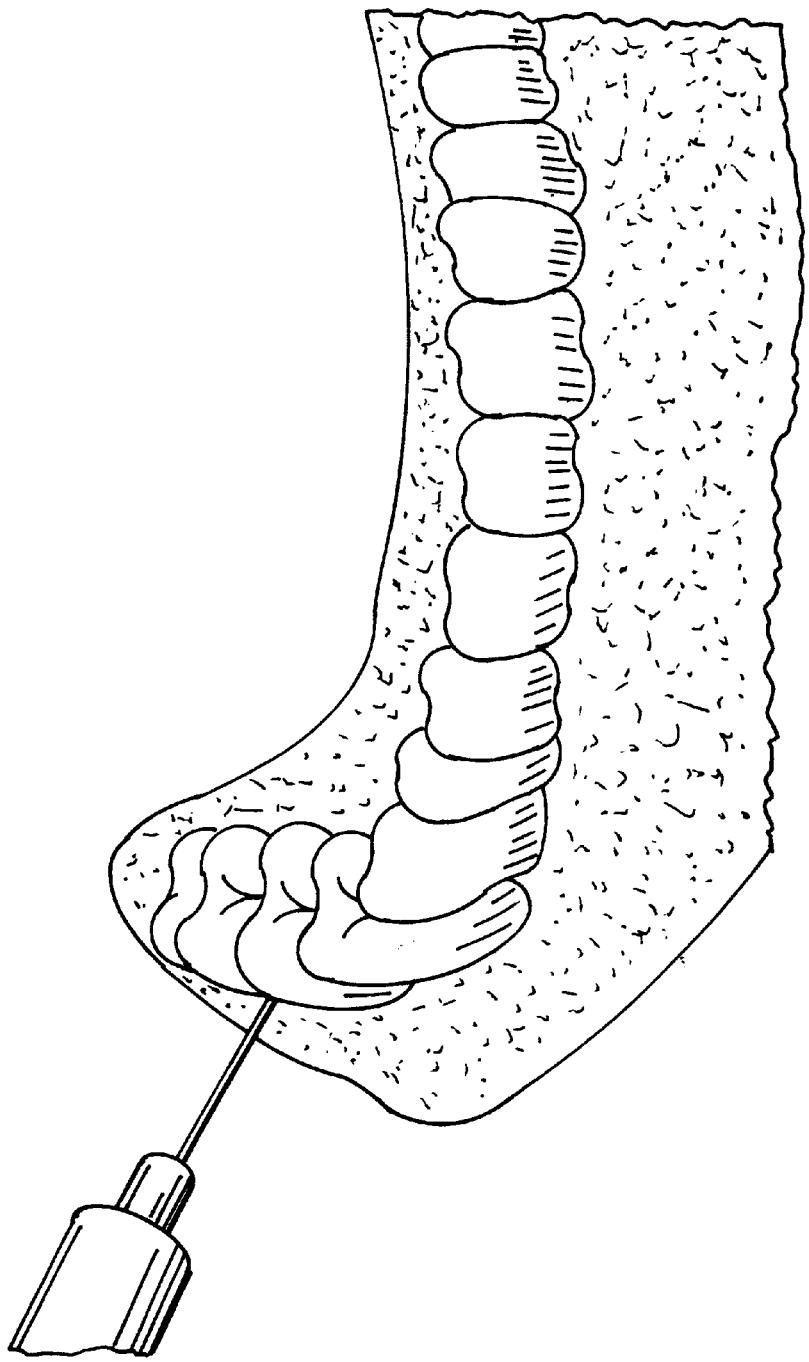
FIG. 6 is a view showing the inclination of the needle.

The use of trepans is generally required in the prior intra-septal technique. In contrast, in the technique of the invention, drills for trepans are not used at all. In the intra-septal technique needle inclination at an angle of 45 degrees to the long axis of the tooth is generally acceptable. In the technique of the invention, a needle inclination of about 30 degrees in case of premolars and 45 degrees in case of molars (FIG. 6) is suggested.

In the prior intra-septal technique, the application speed for the deposition of 1 ml of anesthetic solution, can vary from 10 seconds to 30 seconds.

In the technique of the present invention, for the deposition of 1 ml of anesthetic solution, the time indicated is 3 minutes and 20 seconds, thus the flow rate is much less than that of the intra-septal technique. These figures have been carefully tested with the use of the device of the present invention, resulting in:

1) total absence of pain during the injection, thus more comfort to the patient;
2) absence of post-operative problems. It is known that, in prior subperiosteal techniques, the patient can experience post-operative pain or even tissue necrosis. However, the low controlled delivery velocities employed in the technique of the invention assure the absence of any adverse symptomatology;
3) more security against quick absorption of the anesthetic liquid by blood stream (relative overdosage);
4) longer anesthetic efficiency duration for smaller doses (½ cartridge). Because of the absence of losses caused by reflux, the injection of ½ cartridge is enough for a profound efficient anesthesia, usually lasting over 20 m.

In the technique of the invention, the time spent to fulfil an anesthetic injection will be 3 minutes for the block itself, when the dose used is ½ of the cartridge (in the injection velocity of 0.30 ml/min, i.e. at the fast speed of the injection device disclosed in the aforementioned patent application) after:

1) 15 seconds for the pre-anesthesia (topical) waiting for its effect before placing the needle;
2) 5 seconds to inject some drops of anesthetic liquid, the more superficial the better, in the gingival papilla to form a tiny, slightly ischemic pouch;
3) 15 seconds for the latency of the drug (the needle should be removed from gum during this time);
4) 40 seconds spent on a reinsertion of the needle and its entire course, from the puncture to the bone (at subperiosteal or even intro-osseous). This phase has been remarkable for avoiding pain, using 0.1 ml of anesthetic solution (1/18 cartridge) at a flow rate of 0.15 ml/minute, i.e., at a low speed.

The sum will be approximately 4 minutes for the total anesthetic maneuver.

As the anesthetic symptomatology rapidly establishes, one of the characteristics of this technique is that the work can be initiated immediately after the needle removal so that the work schedule will not be extended.

The attempt to increase the injection speed in order to reduce the time of injection can expose to a danger patients with records of anesthetic contraindication. The gains in safety are huge with the reduced speed and dose procedures set by the technique of the invention.

In comparison, considering the pre-anesthesia maneuvers and the utilization of trepans in the intra-septal technique, the total time of injection will be the same as the proposed technique.

The insertion procedure for the technique of the invention is as follows:

Apply local anesthetic.

Set the injection device for 0.15 ml/minute injection velocity (slow speed setting).

Apply some drops of anesthesia in the gingival papilla until it forms a slight ischemia pouch (the needle in this case should be placed as much as possible parallel to the tissue surface).

Remove the needle and wait 15 seconds (necessary time to achieve drug latency).

Reintroduce the needle slowly, until the bone is contacted and preferably penetrated.

Any pain during the anesthetic application is mainly caused by the rapid increase in the hydraulic pressure put on the tissue by the drug, compressing the bundle of nerves.

During the injection, the professional can make quick interruptions in order to get a total painless application. On feeling pressure, the patient can signal, so that the professional, keeping the position of the needle, can interrupt the application of liquid, in order to wait for the injected volume to settle, thereby avoiding pain. These interruptions should last about 3 seconds. In practice, two or three such interruptions, from the introduction of the needle and the needle's course to the bone, have been experienced.

The entire needle perforation course, from the puncture to the place of the block itself, is supposed to happen slowly so that the drug comes before the penetration of the needle.

Upon touching the cortical plate, the professional should try to perforate it as superficially as possible. The injection device is then set to a flow rate of 0.3 ml/min, (i.e. fast), to complete the application. A dose of ½ cartridge (0.9 ml) is recommended.

The duration of the block achieved by the technique of the invention is similar to the ones reached with the usual infiltration or regional techniques for the mandible, when the proper procedure of the technique has been followed.

In this first technique, the objective is to inject the anesthetic solution in the spongy bone and not in the ligament, as happens in the intraligamentary technique. Because of that, it is recommended that a 30G pediatric needle be used. The 30G needle is more resistant than the conventional short needle (30G short/0.30×21 mm), and thus it has less possibility of bending with the strength applied. Although some makes of extra-short needles can be found on the market, the best results have been obtained with Monoject 30GA extra-short, which is only 10.0 mm long (a bit shorter than the other), and has the best efficiency in the perforation of the osseous plate without causing any damage.

The advantage of this technique lies in the concept of localized block. With this technique, the anesthetic action is restricted to the teeth, and does not anesthetize the buccal or lingual nerves. Therefore, it is a more efficient technique. The intra-osseous technique can be used either for primary anesthesia or for complementary anesthesia, when other local injections have failed to produce the proper anesthesia.

Figure 7:
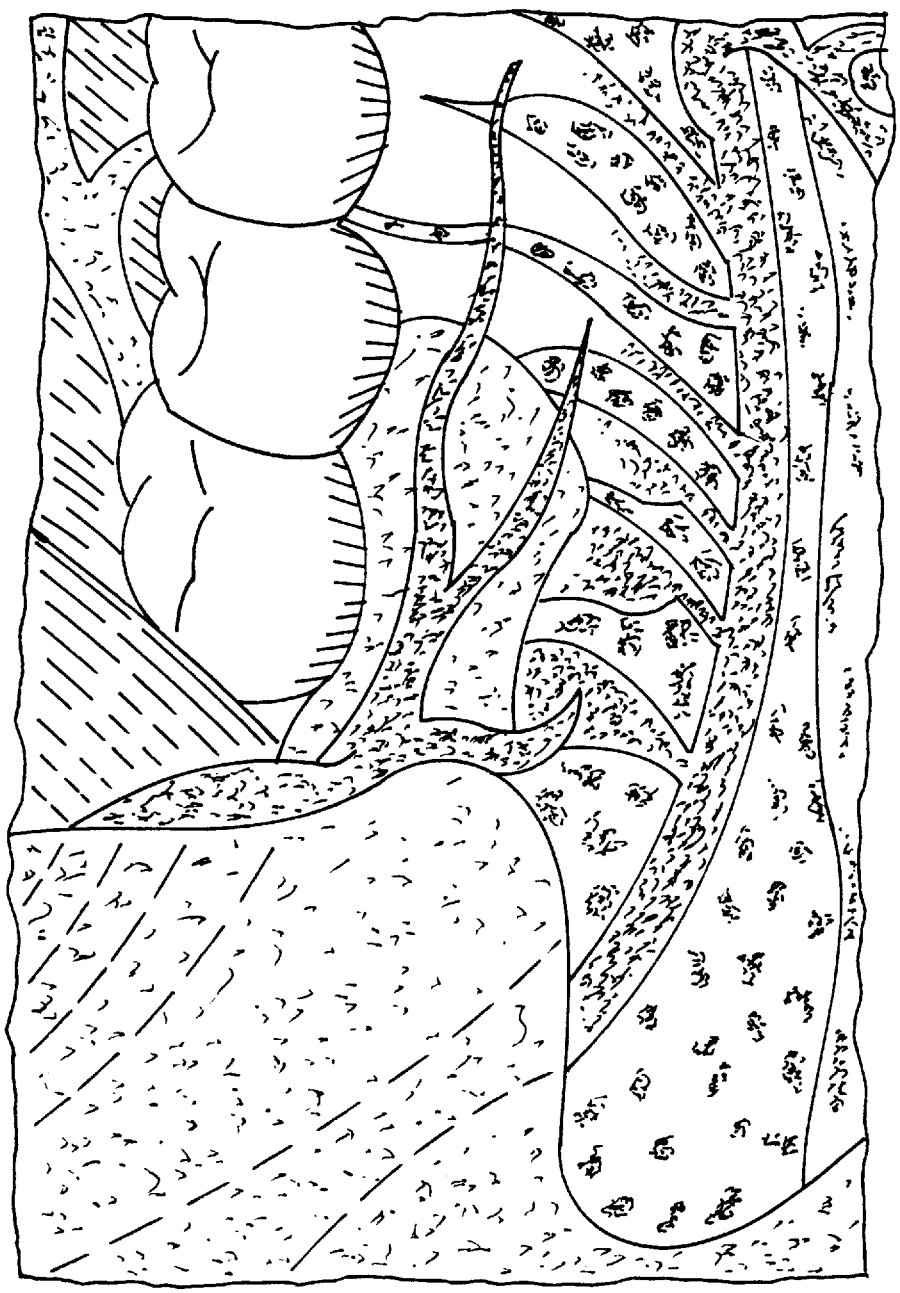
FIG. 7 is a view demonstrating blocking the inferior dental nerve.

In addition, the absence of the unpleasant anesthetic sensation in the lips, tongue, and cheeks offers comfort in dental treatments. By this kind of access, only the inferior dental nerve is blocked (FIG. 7), providing analgesia to the teeth in particular, while avoiding the drug acting in the soft tissue. Anesthetic effects in the tongue and cheeks have been found only in doses over ½ cartridge of anesthetic.

More safety against collateral effects has been obtained thanks to the absolute anesthetic efficacy of doses much smaller than the ones used in conventional techniques, on average between ⅓ and ½ anesthetic cartridge, depending on the patient's weight and the necessary block time required.

The method is an alternative to the use of the inferior alveolar nerve block technique. The method provides more safety in case of molars block. As the anesthetic maneuver in the technique is done through the gingival papilla, this access is safer. The fact that the work is not done in the internal part of the angle of the mandible, a part anatomically dangerous for the high vascularization, and the innervation avoids vascular accidents and the parasthesias by the lesion of the lingual and buccal branches by the needle action (mainly in its removal, in cases its tip has been bent on touching the mandibular remus).

This procedure assures greater safety in children's dentistry and in handicapped or special patients, who get protected from traumatisms by bite. In the traditional way, when there is a need for an inferior alveolar nerve block technique, patients like hemophiliacs are more liable to bleeding caused by accidental bite wounds.

A second embodiment of the improved anesthetic method of the present invention which is suitable to provide anesthetic effect for all the teeth excepting the inferior molars, comprises using a programmable injector to apply a predetermined amount of anesthetic solution below the periosteum without pain and without damage to the periosteal tissue. Specifically the method comprises the following steps: (1) applying a topical anesthetic to the target area of the mucous membrane, (2) setting the programmable injector to a flow rate of about 0.15 ml/min, (3) introducing a superficial injection of anesthetic in the topically anesthetized mucous membrane, (4) stopping the injection and removing the needle, (5) pausing for a period of about 15 seconds, (6) communicating that the patient may experience a slight pressure in the gingival during the remainder of the treatment, (7) inserting the needle through the superficially treated area of the mucous membrane and restarting the injection, (8) inserting the needle, at a steady rate into the tissue below the mucous membrane at a 45 degree angle with respect to the long axis of the tooth, (9) upon a sign from the patient indicating discomfort, pausing the insertion of the needle and pausing the injection of the anesthetic solution for a period of about 3 seconds, (10) upon contact of the needle with the periosteum, repositioning the needle to be parallel to the long axis of the tooth, (10) inserting the needle to the region adjacent the radicular apex, (11) re-programming the flow rate of the programmable injector to a flow rate of about 0.3 ml/min, (12) maintaining the needle position and injector flow rate until a predetermined volume of anesthetic solution has been injected, and (13) withdrawing the needle.

Even though modern local anesthetics are very safe, care must be taken to avoid over-dosages. The physical characteristics and medical history of the patient determine, to a great extent, the effect that a given anesthetic will have on the patient. In addition, the total quantity and rate of injection of the anesthetic can alter the effect of the anesthetic. The method of the present invention, in employing a programmable injector, provides precise control over the quantity and rate of introduction of the anesthetic. Moreover, since the method of the invention introduces the anesthetic in the subperiosteum, less anesthetic is required to produce the desired result. Therefore, in addition to providing painless anesthesia, the method of the present invention minimizes the chances of over-dosage or other negative effects.

Testing has shown that the method of the invention produces uniform and efficacious results throughout the maxilla and the mandible, excluding the inferior molars. Specifically, testing of the method has shown that the following dosage amounts are effective:

| Teeth | Amount |
| --- | --- |
| Anterior maxilla | 0.4 ml (1/4.5 cartridge) |
| Posterior maxilla | 0.6 ml (1/3 cartridge) |
| Anterior mandible | 0.6 ml (1/3 cartridge) |
| Premolar mandible | 0.6 ml (1/3 cartridge) |

For superior molars having very long palatine roots, it is in some cases necessary to complement the anesthetic with a palatine (also subperiosteal) dose of 0.3 ml (1/6 cartridge). In the doses above, it has been clinically observed that the method of the invention produces the same average time of anesthesia as that produced by the traditional carpule (manual needle). In most cases, the anesthetic effect lasted on average 30 to 40 minutes, and in many cases exceeded 1 hour. In cases demanding that anesthesia last longer than 30 minutes, such as endodontic or prosthetic procedures, 0.3 ml may be added to the above doses.

For 30 months, 2500 subperiosteal applications were carried out in regular clinical attendance in the area of dentistry, endodontia, prothesis and ondonto-pediatrics, including all teeth, except the inferior molars. In all the studied cases, the anesthetic was prilocaina 3% with the vasoconstrictor felipressina, which was chosen because it primarily acts on the venous (i.e., return) circulation which avoids a reduction of circulation in the osseous site and possible necrosis. The felipressina produces non-sharp local ischemic effects, accompanied by no hypoxia or cyanosis. Optimal results are received if the anesthetic is used within three months of manufacture, and is stored in a refrigerator. In addition inflamed tissue sites should be avoided because of the considerably altered pH value.

The method of the invention provides that the subperiosteal anesthetic technique may be used as a primary method of anesthesia. The benefits of the method are its ease of application, the absence of pain during the procedure (and concomitant low level of anxiety in the patient), low toxicity due to low dosage, localization of the anesthetic, and faster post-operative recovery.

Through clinical testing of the advanced subperiosteal anesthetic technique of this invention, using a programmable injector of the type described in the above U.S. patent application, it has been discovered that with a slow, steady anesthetic flow rate of about 0.3 ml/min, the entire volume of anesthetic placed below the periosteal layer during subperiosteal injections is integrally absorbed by the bone without anesthetic reflux and with no disjunction or distension of the periosteum. This results in an effective, painless anesthetic procedure which does not traumatize the periosteal conjunctive membrane.

It should be understood, of course, that the specific form of the invention herein illustrated and described is intended to be representative only, as certain changes may be made therein without departing from the clear teachings of the disclosure. Accordingly, reference should be made to the following appended claims in determining the full scope of the invention.

I claim:

1. A method of administering a dental anesthetic, comprising:
   (a) providing an injector device having a needle and a programmable dosage and flow rate;
   (b) programming the flow rate of the injector device to a predetermined rate of about 0.15 ml/min;
   (c) topically anesthetizing the tissue surface in the region of puncture and waiting a few seconds for its effect,
   (d) injecting by hypodermic needle a few drops of anesthetic liquid in the gingival papilla, forming a slightly ischemic pouch,
   (e) removing the needle and waiting a few seconds for the anesthetic to take effect,
   (f) reinserting the needle slowly, over a period of about 40 seconds, while effecting a motor-controlled flow rate of about 0.15 ml/minute of introduction of anesthetic liquid into the tissue, such that the anesthetic liquid precedes and has at least partial effect in the tissue in advance of penetration thereof by said needle,
   (g) contacting, and penetrating the alveolar crest with said needle,
   (h) re-programming the programmable injector for a flow rate of about 0.3 ml/min, and
   (i) thereafter injecting about 0.6 ml to about 0.9 ml of the anesthetic, and liquid by motorized expulsion from said needle, at a constant controlled rate of about 0.3 ml per minute.

2. The method of claim 1 wherein said steps of reinserting the needle and of contacting and penetrating the alveolar crest further comprise inserting the needle substantially through a center of a vertical line interconnecting an apex and a base of a triangle of a gingival papilla.

3. A method of administering a dental anesthetic, comprising:
   (a) providing an injector device having a needle and a programmable dosage and flow rate;
   (b) programming the flow rate of the injector device to a predetermined rate of about 0.15 ml/minute;
   (c) applying a topical anesthetic to the target area of mucous membrane of a patient adjacent a tooth being treated;
   (d) using the programmable injector to introduce a superficial injection of anesthetic in the topically anesthetized mucous membrane;
   (e) stopping the injection and removing the needle;
   (f) pausing for a period of about 15 seconds;
   (g) inserting the needle through the superficially treated area of the mucous membrane and restarting the injection;
   (h) inserting the needle, at a steady rate into the tissue below the mucous;
   (i) upon a sign from the patient indicating discomfort, pausing the insertion of the needle and pausing the injection of the anesthetic solution for a period of about 3 seconds;
   (j) inserting the needle to a region adjacent a radicular apex;
   (k) re-programming the flow rate of the programmable injector to a flow rate of about 0.3 ml/min;
   (l) maintaining the needle position and injector flow rate until a predetermined volume of anesthetic solution has been injected; and
   (m) withdrawing the needle.

4. A method as in claim 3, wherein said step (h) further comprises inserting the needle, at a steady rate, into the tissue below the mucous membrane at a 45 degree angle with respect to a long axis of the tooth.

5. A method as in claim 4, further comprising upon contact of the needle with a periosteum, repositioning the needle to be parallel to the long axis of the tooth.

6. An advanced subperiosteal anesthetic technique, comprising:

(a) applying a topical anesthetic to the target area of mucous membrane of a patient adjacent a tooth being treated;

(b) setting a programmable injector having a needle to a flow rate of about 0.15 ml/min;

(c) using the programmable injector to introduce a superficial injection of anesthetic in the topically anesthetized mucous membrane;

(d) stopping the injection and removing the needle;

(e) pausing for a period of about 15 seconds;

(f) communicating that the patient may experience a slight pressure during the remainder of the treatment;

(g) inserting the needle through the superficially treated area of the mucous membrane and restarting the injection;

(h) inserting the needle, at a steady rate, into the tissue below the mucous membrane at a 45 degree angle with respect to a long axis of the tooth;

(i) periodically pausing the insertion of the needle and pausing the injection of the anesthetic solution for a period of about 3 seconds;

(j) upon contact of the needle with a periosteum, repositioning the needle to be parallel to the long axis of the tooth;

(k) inserting the needle to a region adjacent a radicular apex;

(l) re-programming the flow rate of the programmable injector to a flow rate of about 0.3 ml/min;

(m) maintaining the needle position and injector flow rate until a predetermined volume of anesthetic solution has been injected; and (n) withdrawing the needle.

* * * * *